United States Patent
Pandey et al.

(10) Patent No.: US 10,996,074 B2
(45) Date of Patent: May 4, 2021

(54) ACTIVITY RECOMMENDATION BASED ON A REAL-TIME MAPPING BETWEEN ACTIVITY CHARACTERISTICS AND AUTONOMOUS VEHICLE DYNAMICS

(71) Applicant: International Business Machines Corporation, Armonk, NY (US)

(72) Inventors: Diwesh Pandey, Bangalore (IN); Shiladitya Ghosh, Bangalore (IN); Shashidhar Reddy, Bangalore (IN); Arun Joseph, Kadugodi (IN); Anand Haridass, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 37 days.

(21) Appl. No.: 16/202,599

(22) Filed: Nov. 28, 2018

(65) Prior Publication Data
US 2020/0166373 A1    May 28, 2020

(51) Int. Cl.
| | | |
|---|---|---|
| *G01C 21/36* | (2006.01) | |
| *G06N 5/04* | (2006.01) | |
| *G05D 1/00* | (2006.01) | |
| *A61B 5/16* | (2006.01) | |
| *A61B 5/00* | (2006.01) | |
| *G01C 21/34* | (2006.01) | |

(52) U.S. Cl.
CPC ......... *G01C 21/3697* (2013.01); *A61B 5/165* (2013.01); *A61B 5/6893* (2013.01); *G01C 21/3492* (2013.01); *G05D 1/0088* (2013.01); *G06N 5/04* (2013.01); *G05D 2201/0213* (2013.01)

(58) Field of Classification Search
CPC .................................................. G01C 21/3697
See application file for complete search history.

(56) References Cited

U.S. PATENT DOCUMENTS

| | | | |
|---|---|---|---|
| 9,248,743 B2 | 2/2016 | Enthaler et al. | |
| 9,327,189 B2 | 5/2016 | Bavitz et al. | |
| 9,495,874 B1* | 11/2016 | Zhu | ........................ G08G 1/165 |
| 9,582,004 B2 | 2/2017 | Rothoff et al. | |
| 2013/0253833 A1* | 9/2013 | Tuukkanen | ............ G01C 21/26 |
| | | | 701/538 |
| 2017/0008523 A1 | 1/2017 | Christensen et al. | |
| 2017/0136842 A1 | 5/2017 | Anderson | |
| 2017/0313326 A1 | 11/2017 | Sweeney | |

(Continued)

OTHER PUBLICATIONS

Youtube, https://www.youtube.com/watch?v=Gt3CU0nL3eY. By Leisure Travel Vans channel, 4:39 minutes, Apr. 1, 2016.*

(Continued)

*Primary Examiner* — Anne Marie Antonucci
*Assistant Examiner* — Abadalla A Khaled
(74) *Attorney, Agent, or Firm* — Monchai Chuaychoo

(57) ABSTRACT

An approach for recommending an activity during travel. The approach includes receiving a request for a travel destination and a desired arrival time. Furthermore, the approach determines a route to the travel destination and retrieves external data based on the route. Based on the retrieved data and the route, the approach calculates and outputs an initial activity list. And the approach measures vehicle dynamics based on one or more motion sensors and updates and outputs the activity list based on the vehicle dynamics.

20 Claims, 6 Drawing Sheets

(56) References Cited

U.S. PATENT DOCUMENTS

2018/0107216 A1* 4/2018 Beaurepaire ....... G06Q 30/0261
2019/0162549 A1* 5/2019 Fouad ................. G08G 1/0129

OTHER PUBLICATIONS

Burkhard et al., "Requirements on driving dynamics in autonomous driving with regard to motion and comfort", © Springer Fachmedien Wiesbaden GmbH, ein Teil von Springer Nature 2018 683, M. Bargende, H.-C. Reuss, J. Wiedemann (Hrsg.), 18. Internationales Stuttgarter Symposium, Proceedings, <https://doi.org/10.1007/978-3-658-21194-3_53>, 15 pages.

Kerrigan, Saoirse, "15 of the Most Interesting Patents Acquired in the Past 5 Years", Innovation, <https://interestingengineering.com/15-of-the-most-interesting-patents-acquired-in-the-past-5-years>, 24 pages.

* cited by examiner

ACTIVITY RECOMMENDATION BASED ON A REAL-TIME MAPPING BETWEEN ACTIVITY CHARACTERISTICS AND AUTONOMOUS VEHICLE DYNAMICS

BACKGROUND OF THE INVENTION

The present invention relates generally to the field of transportation, and more particularly to accommodating activities for passengers during travel.

Currently, the active driver is considered as a reference for the development of driving dynamics. However, with the ongoing development of autonomous vehicles, at automation level three according to VDI (Vehicle Driving Institute), the active driver becomes an inattentive passenger. New measurements are needed to be perform on the inattentive passenger, who is not able to anticipate movement of the vehicle, as the passenger did not initiate the maneuver (i.e., a driver solely controls the vehicle). Moreover, the inattentive passengers need to be studied since the passengers may be pursuing other activities during driving. To detect corresponding differences in the vibration behavior experienced by the passenger, a wide variety of positions on the passenger's body needs to be measured. For example, motion sickness occurs when there is a mismatch of the seen (by the passenger) compared to the perceived body movement in the vestibular organ of the passenger. This effect (motion sickness) is particularly stronger when the passenger is reading while being driven. The eyes of the passenger look at the quite stable image of the book, but the body experiences acceleration from the ride.

Depending on the level of attention and the possible new activities of the passengers in an autonomous car, such as reading, sleeping, or working, the requirements for the driving dynamics of vehicles will change as well. So far, different attempts have been made to set these requirements as acceleration limits for the vehicle body derived from studies with conventional cars. In a new approach, acceleration requirements could be derived for the passenger instead of the vehicle body. Thus, in the near future, the vehicle processor may not only control the driving dynamics with respect to the vehicle itself, but also with respect to the activities of the passengers.

SUMMARY

Embodiments of the present invention disclose a method and a computer system for recommending an activity during travel. The method may include one or more computer processors receiving a request for a travel destination and a desired arrival time; determining a route to the travel destination; retrieving external data based on the route; calculating and outputting an initial activity list based on the external data and the route; measuring vehicle dynamics based on one or more motion sensors; and updating and outputting the activity list based on the vehicle dynamics.

According to another embodiment, the computer system for recommending an activity during travel, the computer system comprising: one or more computer processors; one or more computer readable storage devices; and program instructions stored on the one or more computer readable storage devices for execution by at least one of the one or more computer processors, the stored program instructions comprising: program instructions to receive a request for a travel destination and a desired arrival time; program instructions to determine a route to the travel destination; program instructions to retrieve external data based on the route; program instructions to calculate and output an initial activity list based on the external data and the route; program instructions to measure vehicle dynamics based on one or more motion sensors; and program instructions to update and output the activity list based on the vehicle dynamics.

DETAILED DESCRIPTION

Figure 1:
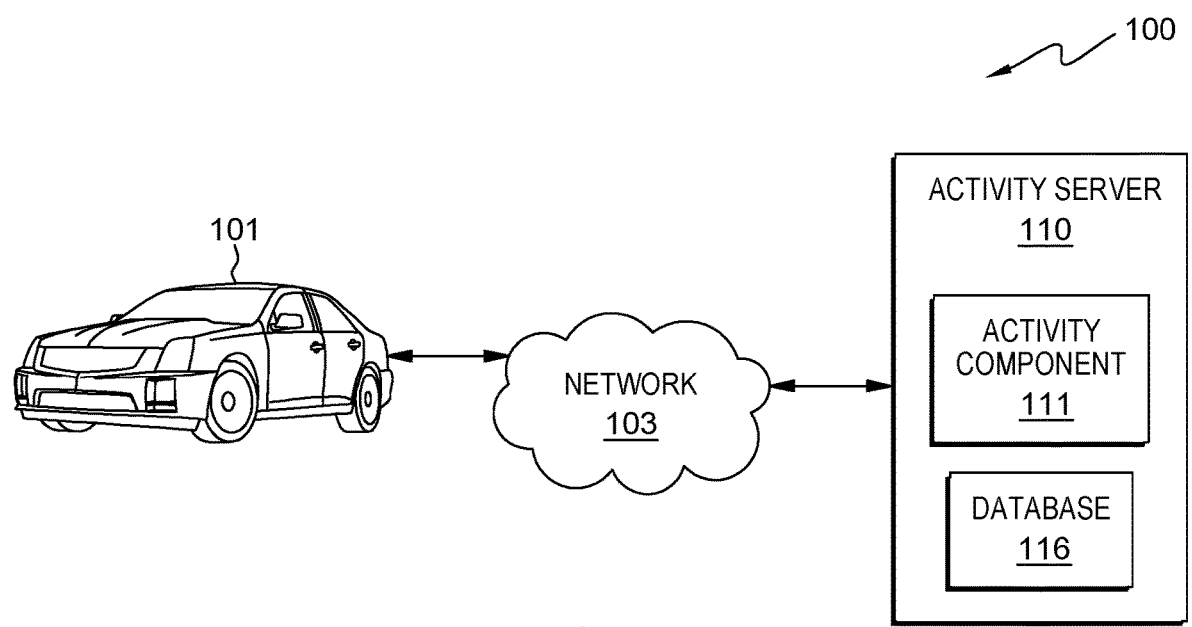
FIG. 1 is a functional block diagram illustrating the activity vehicle environment, designated as 100, in accordance with an embodiment of the present invention.

Embodiments of the present invention recognize that improvements in engaging in various activity/tasks while riding in a vehicle (autonomous or non-autonomous) can be enhanced. Particularly, performing a task inside a vehicle while the vehicle is in motion and subjected to real-time vehicle dynamics. The present invention can propose a sorted list of tasks to the user/passengers that ensures an improved overall user-experience during the trip.

The interiors of an autonomous vehicle of the future may be drastically different from the current setup of traditional cars. Interior of traditional cars are setup to allow the driver to steer the vehicle and nothing more. However, the vehicles of tomorrow may be synonymous to a living-space on wheels, capable of supporting day-to-day activities. For example, activities like office work, leisure activities (e.g., reading and writing), entertainment (e.g., gaming, movies, etc.), dining, physical exercise (e.g., jogging, rowing, etc.).

One key problem in supporting activities (e.g., leisure activities, entertainment, dining, etc.) in future vehicles is that passengers are constantly subjected to movements (e.g., vertical, lateral, to-and-fro, etc.) as the vehicle moves along its route in the presence of traffic over different road conditions. Such movements make it difficult (or infeasible) to perform certain tasks comfortably at a certain point of time. For example, the task of drinking a beverage is difficult in the presence of constant vertical jerking movements as there are chances of spilling the liquid in the process. Or similarly a task like using a jogging/running can be difficult (or can be prone to injuries) in the presence of lateral movements caused by vehicle navigating through traffic in speed as it makes it difficult for the user to stand upright.

Additionally, other vehicle dynamics (constraints) can limit overall activities. For example, energy consumption while performing different tasks is another factor that may be considered. Some tasks which are be power-hungry (and degrade the overall performance of the vehicle over the time). For example, running on a powered treadmill (or rowing machine) would be a task that requires a considerable amount of energy from the vehicle and would deplete the energy reservoir of the vehicle over the duration of trip.

The embodiment of the present invention can be realized with the use of a real-time mapping method and systems between the list of activity characteristics and the vehicle dynamics. The list of activities can be qualified by a set of constraints which are mapped to the movement of a vehicle. The constraints can include the following but is not limited to, a list of activities with certain energy consumption rates, a list of activities modeled for a selected route and estimated time of arrival to the destination. Furthermore, these constraints are used to calculate an activity model and output a sorted activity (e.g., task list, etc.) to enhance the experience of the user during the trip. Furthermore, as the vehicle moves, the sorted activity is re-shuffled based on real-time vehicle dynamic data. For example, depending on the trip, users may start the trip off by reading a book but eventually takes a nap when the road condition becomes too bumpy to read. Conversely, the passenger may start of working on the laptop and eventually is able to do some light exercise.

Detailed description of embodiments of the claimed structures and methods are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

The term "passenger", is used interchangeably with the term "user", "driver" and "traveler", as used herein refers to the person being transported by an automobile, a bike, an airplane, a boat, or any other vehicle (autonomous or non-autonomous).

The term "activities", is used interchangeably with the term "task", as used herein refers to the "job" or "chore" as performed by the passenger during travel. This can include office work, leisure activities (e.g., reading and writing), entertainment (e.g., gaming, etc.), dining and physical exercise.

FIG. 1 is a functional block diagram illustrating the activity vehicle environment, designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Activity vehicle environment 100 includes vehicle 101 and activity server 110, all interconnected over network 103.

Vehicle 101 in the present embodiment is the vehicle utilized by the user. Vehicle 101 can be a multi-wheel vehicle (e.g., motorcycle, passenger cars, bus, etc.). Vehicle 101 can also be a vehicle without any wheels and may rely on other methods of propulsion (e.g., magnetic, etc.). Vehicle 101 can be equipped with various sensors (e.g., speed, rotation, steering angle, lateral acceleration, vertical axis, etc.) to measure vehicle dynamics as well as other non-vehicle related sensors (e.g., heart rate tracker, facial recognition, etc.) to measure the passenger cognitive state (e.g., happy, sad, sleepy, angry, tired, etc.). For example, a camera system can recognize facial expressions to determine the mood of the user. A user is yawning can be indicative of the boredom or tiredness by the user.

Network 103 can be, for example, a telecommunications network, a local area network (LAN), a wide area network (WAN), such as the Internet, or a combination of the three, and can include wired, wireless, or fiber optic connections. Network 103 can include one or more wired and/or wireless networks that are capable of receiving and transmitting data, voice, and/or video signals, including multimedia signals that include voice, data, and video information. In general, network 103 can be any combination of connections and protocols that can support communications between activity server 110 and other computing devices (not shown) within activity vehicle environment 100.

Activity server 110 can be a standalone computing device, a management server, a web server, a mobile computing device, or any other electronic device or computing system capable of receiving, sending, and processing data. In other embodiments, activity server 110 can represent a server computing system utilizing multiple computers as a server system, such as in a cloud computing environment. In another embodiment, activity server 110 can be a laptop computer, a tablet computer, a netbook computer, a personal computer (PC), a desktop computer, a personal digital assistant (PDA), a smart phone, or any other programmable electronic device capable of communicating other computing devices (not shown) within 100 via network 103. In another embodiment, activity server 110 represents a computing system utilizing clustered computers and components (e.g., database server computers, application server computers, etc.) that act as a single pool of seamless resources when accessed within activity vehicle environment 100. In yet a further embodiment, activity server 110 can be embedded/integrated with a vehicle. For example, activity server 101 can reside on vehicle 101. In general, activity server 110 provides the ability to recommends and update activities list for users during the trip. Activity server 110 includes activity component 111 and database 116.

Activity component 111 of the present invention provides the capability of recommending an initial activity list before departure and updating the initial activity list during travel for passengers. Furthermore, activity component 111 can learn, through deep learning techniques (e.g., artificial intelligence, neural network, etc.), the habits and propensity (including the cognitive state) of the user and able to deduce a list of favorite activities of the user while traveling (e.g., current route or past travels). For example, activity component 111 can recognize that Brett likes to read the news headlines while drinking his coffee as soon as he gets into the vehicle. Conversely, activity component 111 can recognize that Viktoria enjoys solving 3D puzzles while in the car.

Database 116 is a repository for data used by access activity component 111. A database is an organized collection of data. Database 116 can be implemented with any type of storage device capable of storing data and configuration files that can be accessed and utilized by activity server 110, such as a database server, a hard disk drive, or a flash memory. Database 116 uses one or more of a plurality of techniques known in the art to store a plurality of information. In the depicted embodiment, database 116 resides on activity server 110. In another embodiment, database 116 may reside elsewhere within 100, provided that activity component 111 has access to database 116. For example, database 116 can reside on vehicle 101. Database 116 may store information associated activities of the passenger. For example, Rob, likes to meditate during travel.

Figure 2:
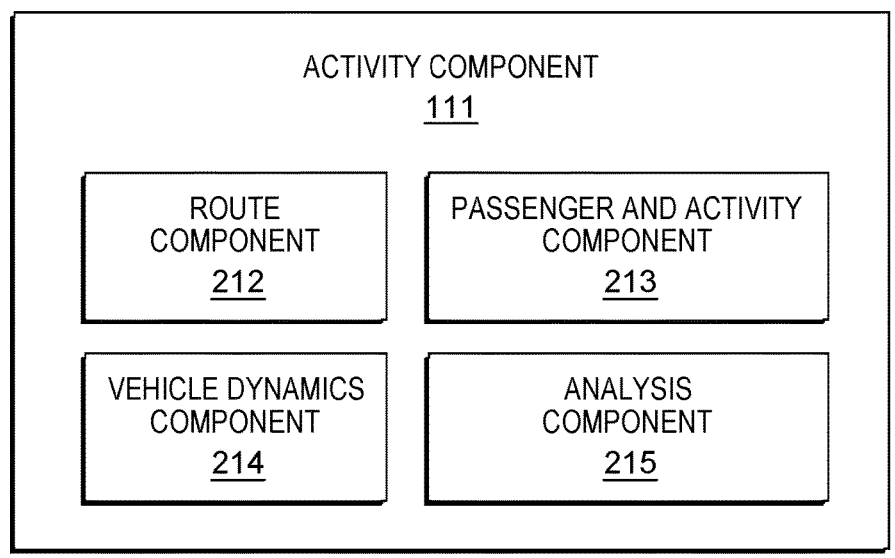
FIG. 2 is a functional block diagram illustrating the individual components of activity component 111 residing in activity vehicle monitoring environment in accordance with an embodiment of the present invention.

FIG. 2 is a functional block diagram illustrating the individual components of activity component 111 residing in activity vehicle environment 100 in accordance with an embodiment of the present invention. Activity component 111 includes route component 212, passenger and activity component 213, vehicle dynamics component 214 and analysis component 215.

Route component 212 of the present invention provides the capability of identifying the location of the user and the several routes to the final destination from a starting point or current location of the user. Route component 212 can determine the shape and path of the trip and ascertain various road characteristics such as radius of the road bend/curves, the degree of incline of the path and road surface imperfections. For example, route component 212 can rely on sensors to detect upcoming road imperfections or curves. Route component 212 can determine the road geometry based on retrieved road maps. In addition, route component 212 can gather traffic-related and weather-related information along the route. It is noted that the source for route component 212 can be an emergency broadcast (e.g., weather emergency) station or from online databases (e.g., traffic websites, etc.). It is further noted that route component 212 can share road conditions with DOT (Department of Transportation) along a particular route based on the sensors (e.g., cameras, sound-based proximity sensors, light-base proximity sensors, radio frequency-based sensors, etc.) on the vehicle. For example, the imperfections of the road conditions can be transmitted to DOT for future road repairs as vehicle 101 is traveling along a route based on the input passenger.

Passenger and activity component 213 of the present invention provides the capability of storing and retrieving a list of vehicle related activities/tasks for a trip. For example, list of activities can include, but it is not limited to, activities like office work, leisure activities (e.g., reading and writing), entertainment (e.g., gaming, etc.), dining, physical exercise (e.g., running, rowing, etc.). In addition, passenger and activity component 213 can store and retrieve preference of users on performing those activities and tasks (e.g., historical patterns, etc.). For example, the system can recall via passenger and activity component 213 that Joe enjoys reading during a trip. The vehicle can suggest that favorite task (i.e., reading) based on recognizing the user, Joe, is inside the vehicle. Passenger and activity component 213 can store and retrieve preferences of the user, activities associated with a trip from database 116. It is noted that the list of activities can be adjustable and selectable by the user.

Vehicle dynamics component 214 of the present invention provides the capability of detecting and measuring forces subjected on the vehicle while vehicle is in motion. Vehicle dynamics component 214 can retrieve data from various sensors throughout the vehicle that detect various forces. Sensors can be embedded throughout the vehicle including the seats belonging the passenger. For example, the sensor can detect the acceleration or deceleration along all the major axis (e.g., x, y and z). These forces will be discussed in greater in details regarding FIG. 3A and FIG. 3B.

Additionally, vehicle dynamics component 214 can also ascertain the cognitive state of the users in the vehicle based on data from various sensors. For example, the sensors can include cameras for capturing facial expression of the passenger. Furthermore, sensors can also detect the physiological state of the passenger such as a heart rate and blood pressure.

Analysis component 215 of the present invention provides the capability of recommending activities/tasks for a user based on data from route component 212, passenger and activity component 213 and vehicle dynamics component 214. Analysis component 215 determines an initial list of activities at the start of the car trip and dynamically adjust the list based on but is not limited to, a change in road conditions, an activity energy consumption, a time to arrive at destination and a change in vehicle dynamics. It is noted that analysis component 215 dynamically adjust the list based on a user selectable activity window. It is not feasible to re-sort and re-shuffle the activity list every second based on changing conditions. Therefore, an activity window (i.e., time based), that is adjustable by the user or the system, is used while the vehicle is motion. The activity window can be several minutes or several hours depending selection by the user or system and the estimated time to destination. For example, an activity window for a trip from Los Angeles to San Diego can be 10 minutes. However, an activity window for a 15-mile trip from the residence of the passenger to work can be one minute.

Figure 3A:
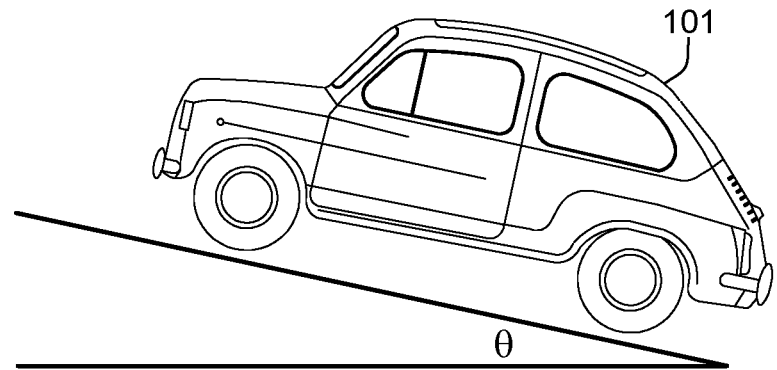
FIG. 3A and FIG. 3B illustrates vehicle dynamic parameters as a side profile and in 3D space, respectively, in accordance with an embodiment of the present invention.
Figure 3B:
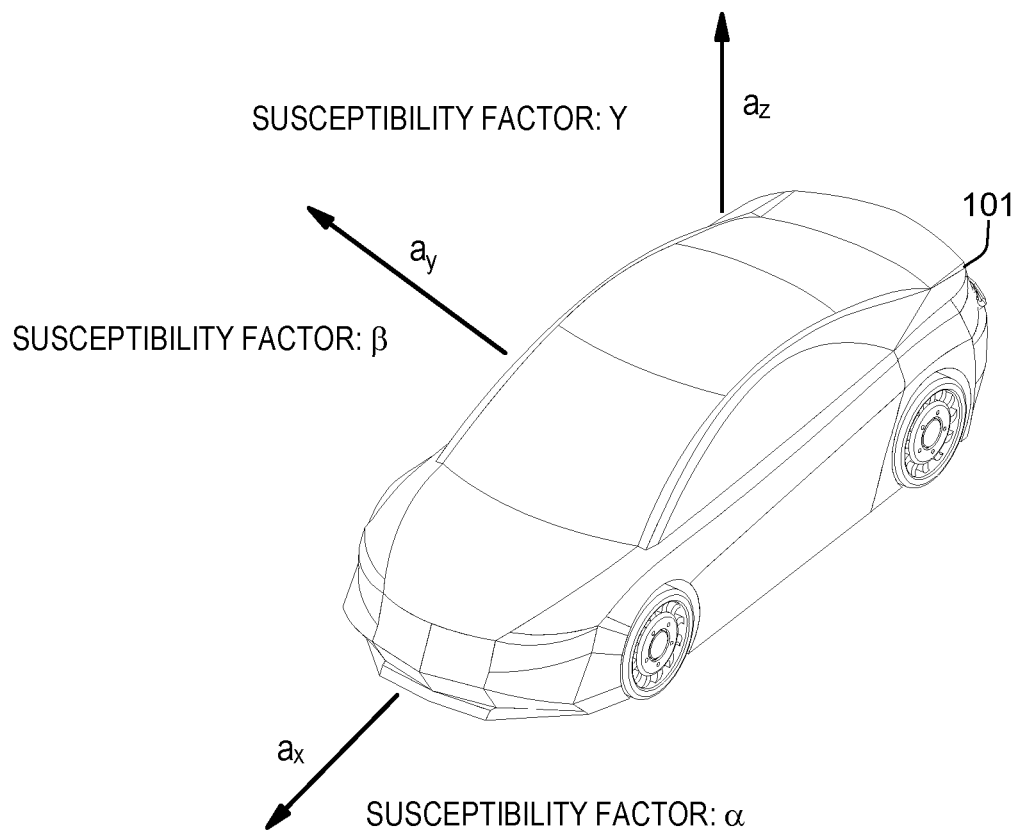

FIG. 3A and FIG. 4B illustrates the various forces subjected on the vehicle during the trip. These forces are measured by various sensors located throughout the vehicle. Definition of vehicle dynamics will be explained further below. The movements experienced by passengers are from inside the vehicle, the vehicle dynamics is measured by the acceleration of the moving vehicle along the three axes:

Acceleration along X axis ($a_x$): Caused by frequent acceleration and braking (to-and-fro)

Acceleration along Y axis ($a_y$): Caused by steering movements (lateral)

Acceleration along Z axis ($a_z$): Caused by road disturbances (vertical)

The activities that can be performed inside the vehicle can also characterized based on their susceptibility to different movements inside the vehicle and the gradient of the road surface. The following algorithm can be used to quantify the movement inside the vehicle in terms of its dynamics:

$$\text{Total movement}(T) = \alpha^* |a_x| + \beta^* |a_y| + \gamma^* |a_z| + \Delta^* \sin\theta$$

where $\alpha$, $\beta$ and $\gamma$ are the susceptibility factors for a particular activity for movements along the axes X, Y and Z respectively. $\Delta$ is the susceptibility factor for the gradient ($\theta$) of the surface. These factors are calculated before-hand and are static in nature.

The objective of the overall system (i.e., activity component 111) is to sort the list of activities based on the minimum value of T calculated from the estimated real-time values of $a_x$, $a_y$ and $a_z$, and the gradient of the road surface associated with the route to be traveled and the estimated time arrival (ETA) to be met.

The forces (on the vehicle) previously mentioned are used to calculate the susceptibility factors. The susceptibility factors of an activity are directly related to its characteristics. Different activities are difficult to perform in the presence of different types of movement. The activities can be modeled by using the susceptibility factors in the following paragraphs.

The activities that are more difficult to perform in the presence of constant vertical jerking movements is going to have $\alpha > \beta$. Meaning that the vertical movements are going to contribute more towards the total movement (T) inside the vehicle. For example, drinking a beverage inside a moving vehicle is more difficult in the presence of vertical movements as there are more chances of spilling the liquid that way. Conversely, lateral movements do not have such an adverse effect as even with minor lateral movements, the liquid still remains within the walls of the container.

Similarly, the activities that are more difficult to perform in the presence of lateral movement is going to have $\beta > \alpha$. Meaning that the vertical movements are going to contribute more towards the total movement (T) inside the vehicle. For example, writing on paper is substantially difficult in the presence of constant lateral movements that can easily be caused by high-sped turns to maneuver through traffic. Consequentially, the vertical movements have a lesser effect as long as they are not large in magnitude Any activity that requires standing becomes difficult to perform when the gradient of the road surface is greater than a certain threshold. For all such tasks, $\Delta$ contributes greatly to the total movement (T) as it is multiplied with sine of the angle of the gradient. For example, running on a treadmill is certainly one of the tasks that will be affected by the gradient of the road surface. Furthermore, as the vehicle is on an incline (flyovers, underpasses etc.) it is just not possible to stand up-right.

Figure 4:
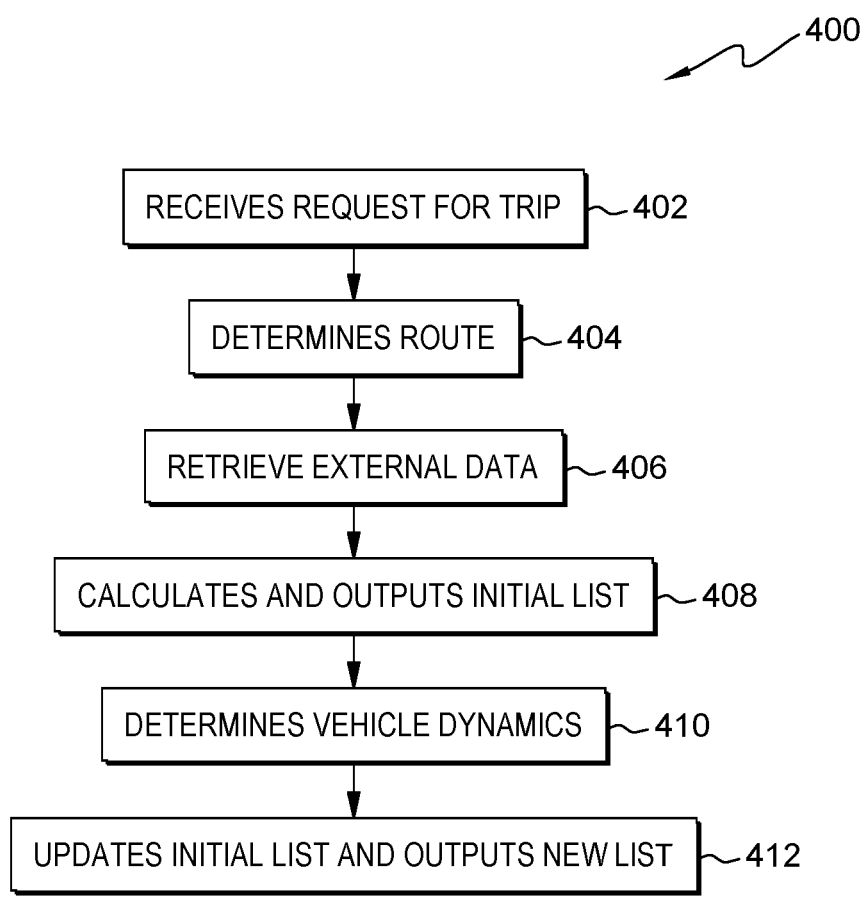
FIG. 4 is illustrating the steps executing the activity component 111 designated as 400, in accordance with a different embodiment of the present invention.

FIG. 4 is a flowchart illustrating the activity travel, designated as 400, in accordance with an embodiment of the present invention.

Activity component 111 receive a request for the trip (step 402). In an embodiment, the passenger invokes activity component 111 by opening the application. For example, the passenger requests a destination via the application on a mobile device. The passenger presses the start feature of the application to request the trip. In another embodiment, activity component 111 is invoked automatically without passenger interaction by sensors detecting voice commands. For example, the passenger enters the vehicle and the passenger speaks the destination to activity component 111.

In another embodiment, passenger may input a certain time to reach the destination. This can be used by activity component 111 to calculate the list of activities given that time requested by the passenger. It is noted that the passenger can enter the required time into the application on mobile device (connected to the vehicle), on the screen of the vehicle or speak the required time to the vehicle.

In an alternative embodiment, activity component 111 may accept a desired activity input from the passenger in addition to the destination and desired time to destination. The desired activity may be requested through the application on a mobile device or vehicle passenger interface. It is noted that application on a mobile device is linked to the vehicle processing unit.

Activity component 111 determines the route of the trip (step 404). In an embodiment, activity component 111 through route component 212 calculates the route to the destination based on the passenger inputs (destination and time to destination) from the previous step (step 402). Based on the identified intended travel destination of the traveler, route component 212 can create several routes from the current destination to the intend destination. However, activity component 111 will narrow down the routes to just one route based on activities, road conditions, weather-related information and desired initial activity.

Activity component 111 retrieves external data for the trip (step 406). In an embodiment, activity component 111 through route component 212 would retrieve the current road conditions (e.g., public APIs), weather conditions and traffic conditions.

Activity component 111 calculates and output initial list (step 408). In an embodiment, activity component 111 through analysis component 215 calculate an initial list of activities for the passenger before the trip. Activity component 111 uses the following factors and parameters to calculate the initial activity list. These factors and parameters includes, but is not limited to, enumerating all possible routes from start to the destination, determining the minimum average speed to meet the ETA (estimated time of arrival that was requested by the passenger), determining the road profiles (e.g., gradients, number of bend/curves, etc.), estimating the acceleration along the three or more axes ($a_x$, $a_y$, $a_z$ and $\theta$) and initial value of T based on the available respective activities. Additionally, activity component 111 can calculate the total movement (T) based on the initial estimated values of acceleration and the known susceptibility coefficients for each activity. Furthermore, activity component 111 can calculate the power requirement of each task and can downgrade the power-hungry tasks based on the present energy-level of the vehicle. For example, Joe would like to travel from his house to his work, activity component 111 recommends a few activities (e.g., reading and responding to work emails) that are acceptable along the given route. Activity component 111 presents this initial list to Joe before the commence of travel.

In an alternative embodiment, if the passenger has entered a desired activity at the beginning of the trip, activity component 111 can reject the passenger's desired activity based adverse road and weather conditions and length of the trip. For example, Rob wishes to drink his tea from home to his brother's house (3 miles away). However, based on the road condition and distance of the trip, Rob will not be able to drink his tea due to the fact the trip will take less than one and half minutes. Therefore, activity component 111 can suggest an alternate activity to Rob for the trip, such as resting or listening to the news. Conversely, if Rob request the activity of watching his sitcom from his house to the airport, which is locate 40 miles away from Rob, then activity component 111 can accommodate his initial activity request. It is noted that the desired activity may be requested through the application on a mobile device or vehicle passenger interface. It is further noted that application on a mobile device is linked to the vehicle processing unit.

Activity component 111 determines the vehicle dynamics (step 410) during travel. In an embodiment, activity component 111 through vehicle dynamics component 214 can determine the new values of T and susceptibility factors based on the changing road conditions. Additionally, activity component 111 through route component 212 can retrieve real-time traffic data along the current route.

Activity component 111 updates the list and outputs a new list (step 412). Based on the updated data from route component 212, present energy consumption level of the vehicle and the real-time data from vehicle dynamics component 214, analysis component 215 can calculate and update a new activity list. For example, Joe was answering his email at the start of the trip but due to changing road conditions (i.e., bumpier), activity component 111 recommends that Joe relaxes to soothing music for the remainder of the trip. It is noted that activity component 111 updates the activity list within an activity window based on the changing road conditions, the cognitive state of the passenger and power consumption of the activity. For example, Joe becomes tired of answering his work email, activity component 111 detects the change in cognitive state of Joe and recommends a new activity such as sleeping.

Figure 5A:
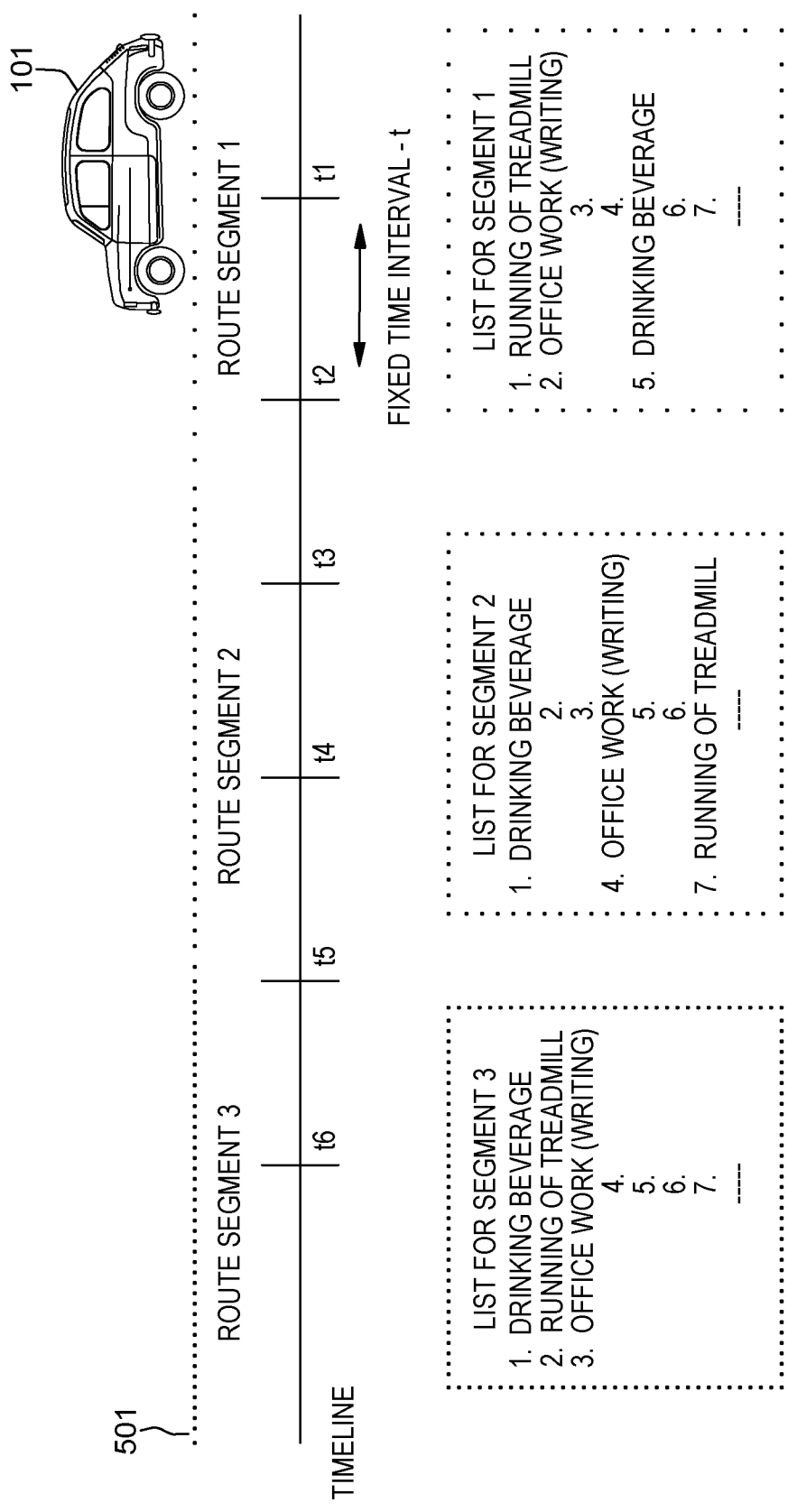
FIG. 5A is a time line illustrating activities available during the initial start of the trip in accordance with an embodiment of the present invention.

FIG. 5A is a time line illustrating activities available during the initial start of the trip in accordance with an embodiment of the present invention. Timeline 501 of FIG. 5A list the following initial activities: running on treadmill, office work and drinking beverages at $t_1$ and route segment 1. Based on the route condition, activities recommended for route segment 1 includes running and office work. Both tasks are ranked respectively 1 to 2. The activity list for route segment 2 based on $t_1$ includes ranking beverage at 1 but office work at 4. The list is calculated based on the initial estimations as described in the step 408 of FIG. 4. It is noted that at each time interval t, data from the sensors located throughout the vehicle is read for real-time parameters (e.g., accelerations on three different axes, etc.).

Figure 5B:
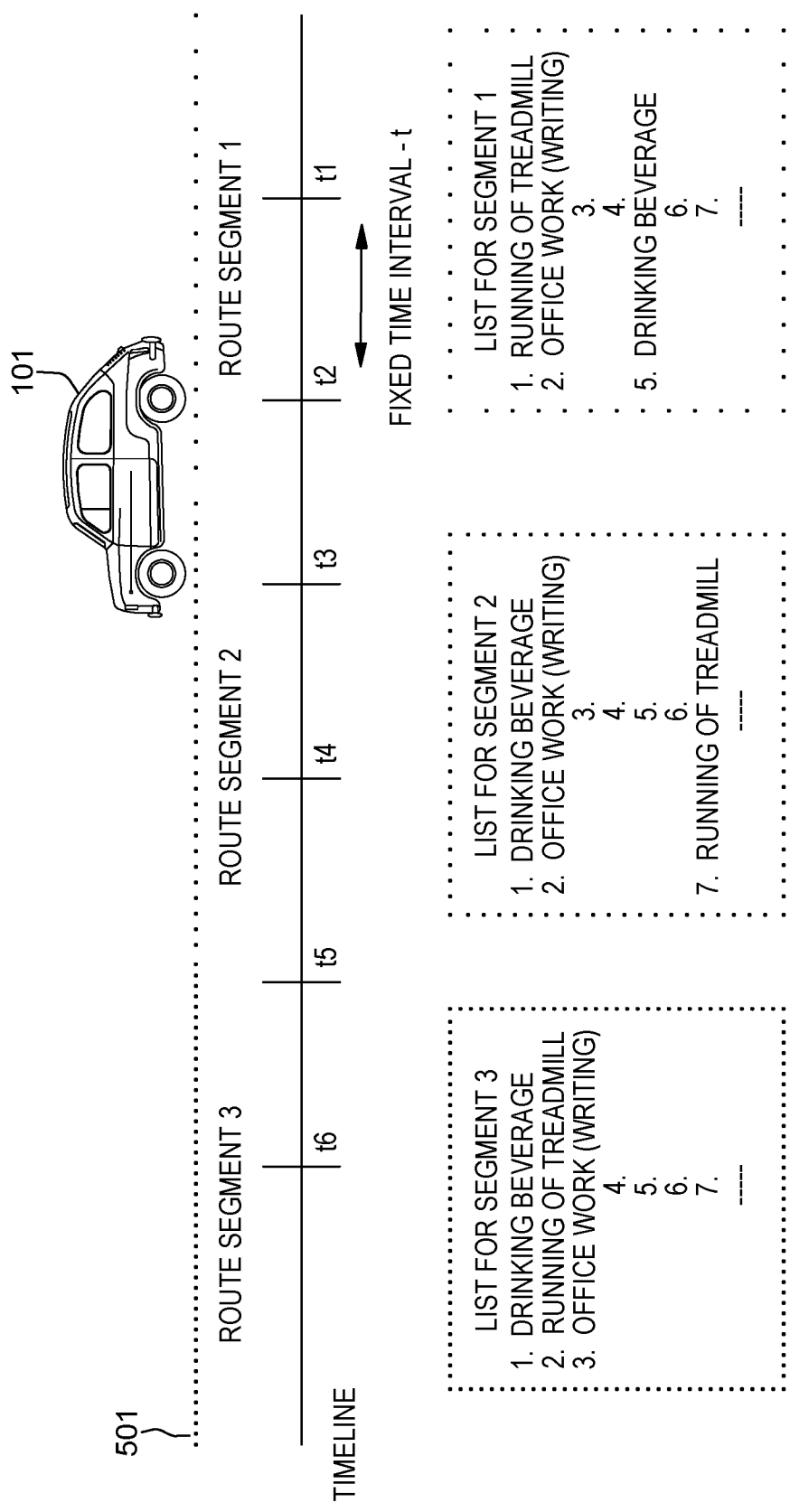
FIG. 5B is a continuation of the time line from FIG. 4A but illustrating changing activities available during of the trip in accordance with an embodiment of the present invention.

FIG. 5B is a continuation of the time line from FIG. 4A but illustrating activities available during of the trip in accordance with the same embodiment of the present invention. Timeline 501 from FIG. 5A, shows vehicle 101 moving from $t_1$ (initial start time) and route segment 1 to route segment 2 at $t_2$ and $t_3$. Assuming that the road conditions are ideal (e.g., smooth and not rough, etc.), activities such as office work can be ranked higher from previous estimate (i.e., from 4 to 2).

Figure 6:
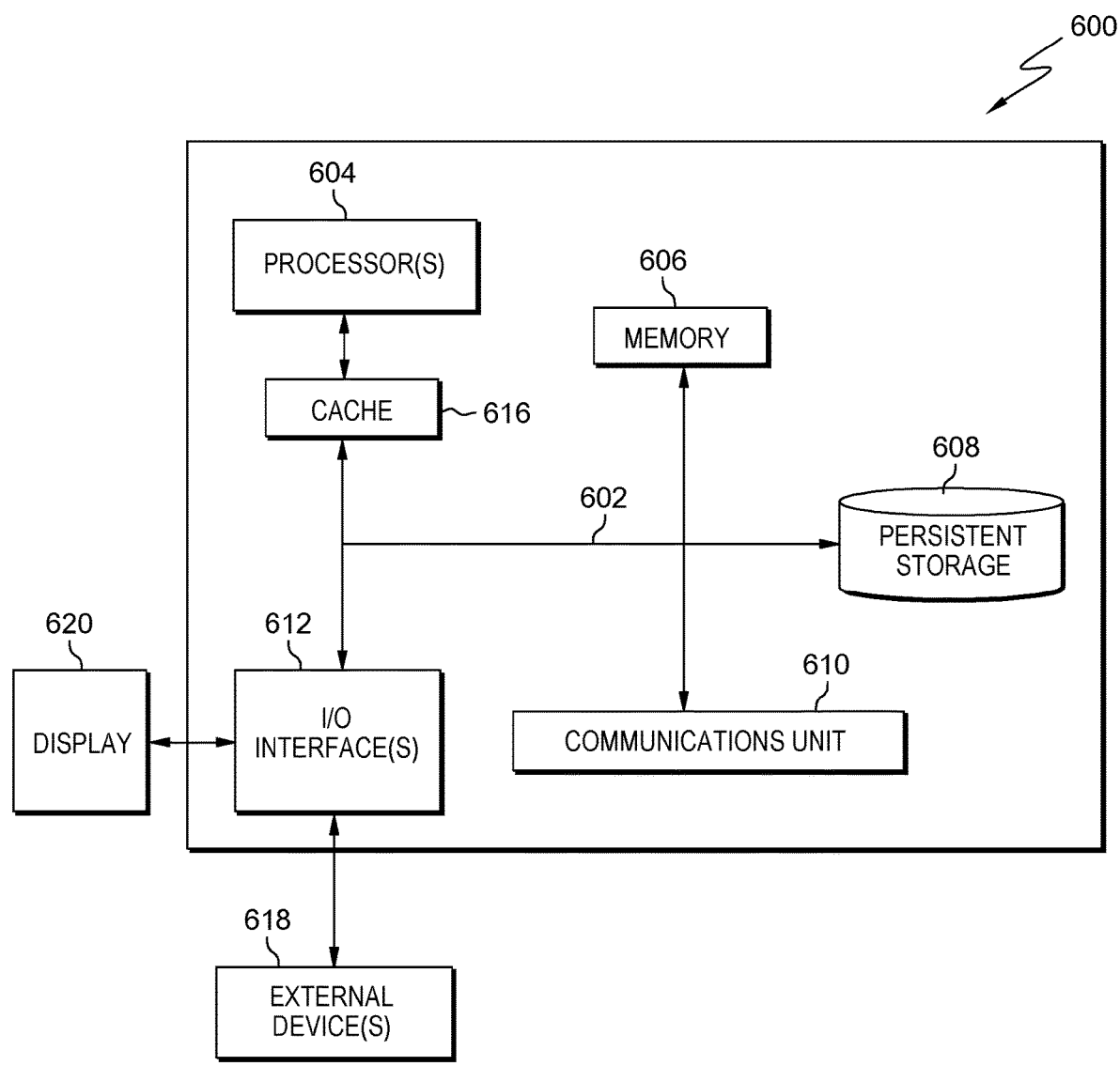
FIG. 6 depicts a block diagram, designated as 600, of components of the server computer executing the program within the activity vehicle environment, of FIG. 1A, in accordance with an embodiment of the present invention.

FIG. 6 depicts a block diagram, designated as 600, of components of the server computer executing the program within the vehicle activity environment, of FIG. 1, in accordance with an embodiment of the present invention.

Activity server 110 can include processor(s) 604, cache 616, memory 606, persistent storage 608, communications unit 610, input/output (I/O) interface(s) 612 and communications fabric 602. Communications fabric 602 provides communications between cache 616, memory 606, persistent storage 608, communications unit 610, and input/output (I/O) interface(s) 612. Communications fabric 602 can be implemented with any architecture designed for passing data and/or control information between processors (such as microprocessors, communications and network processors, etc.), system memory, peripheral devices, and any other hardware components within a system. For example, communications fabric 602 can be implemented with one or more buses.

Memory 606 and persistent storage 608 are computer readable storage media. In this embodiment, memory 606 includes random access memory (RAM). In general, memory 606 can include any suitable volatile or non-volatile computer readable storage media. Cache 616 is a fast memory that enhances the performance of processor(s) 607 by holding recently accessed data, and data near recently accessed data, from memory 606.

Program instructions and data used to practice embodiments of the present invention, e.g., activity component 111 and database 116, can be stored in persistent storage 608 for execution and/or access by one or more of the respective processor(s) 607 of activity server 110 via memory 606. In this embodiment, persistent storage 608 includes a magnetic hard disk drive. Alternatively, or in addition to a magnetic hard disk drive, persistent storage 608 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 608 may also be removable. For example, a removable hard drive may be used for persistent storage 608. Other examples include optical and magnetic disks, thumb drives, and smart cards that are inserted into a drive for transfer onto another computer readable storage medium that is also part of persistent storage 608.

Communications unit 610, in these examples, provides for communications with other data processing systems or devices, including resources of activity server 110. In these examples, communications unit 610 includes one or more network interface cards. Communications unit 610 may provide communications through the use of either or both physical and wireless communications links. Activity component 111 and database 116 may be downloaded to persistent storage 608 of activity server 110 through communications unit 610.

I/O interface(s) 612 allows for input and output of data with other devices that may be connected to activity server 110. For example, I/O interface(s) 612 may provide a connection to external device(s) 618 such as a keyboard, a keypad, a touch screen, a microphone, a digital camera, and/or some other suitable input device. External device(s) 618 can also include portable computer readable storage media such as, for example, thumb drives, portable optical or magnetic disks, and memory cards. Software and data used to practice embodiments of the present invention, e.g., activity component 111 and database 116 on activity server 110, can be stored on such portable computer readable storage media and can be loaded onto persistent storage 608 via I/O interface(s) 612. I/O interface(s) 612 also connect to a display 620.

Display 620 provides a mechanism to display data to a user and may be, for example, a computer monitor or the lenses of a head mounted display. Display 620 can also function as a touchscreen, such as a display of a tablet computer.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for recommending an activity during travel by an autonomous vehicle, the method comprising: receiving a request for a travel destination and a desired arrival time for a traveler on an autonomous vehicle;

determining a route to the travel destination; retrieving external data based on the route; calculating and outputting an initial activity list based on the external data, energy consumption rate of the autonomous vehicle as required by each individual activity as part of the initial activity list, habit and propensity of the traveler and the route, wherein the initial activity list consists of jogging, rowing and running; measuring vehicle dynamics based on one or more motion sensors of an autonomous vehicle; and updating the initial activity list and outputting an updated initial activity list based on the vehicle dynamics, energy consumption rate of the autonomous vehicle as required by each individual activity as part of the updated initial activity list and changing road conditions.

2. The method of claim 1, wherein determining the route to the travel destination further comprises:
retrieving one or more routes to the travel destination; and
selecting one route from the one or more routes based on the desired arrival time.

3. The method of claim 1, wherein retrieving external data further comprises of weather-related, traffic related and road conditions.

4. The method of claim 1, wherein calculating and outputting the initial activity list further comprises:
determining the initial activity list based on one or more susceptibility factors, the external data and the desired arrival time; and
outputting the initial activity list to one or more users.

5. The method of claim 4, wherein the one or more susceptibility factors further comprises of $\alpha$, $\beta$ and $\gamma$ wherein are $\alpha$, $\beta$ and $\gamma$ are the one or more susceptibility factors for the activity list associated movements along X, Y and Z axes, respectively.

6. The method of claim 1, wherein measuring the vehicle dynamics further comprises:
retrieving data from one or more sensors wherein the one or more sensors are capable of detecting forces along x, y and z axis of the vehicle.

7. The method of claim 1, wherein updating the initial activity list and outputting the updated initial activity list based on the vehicle dynamics further comprises:
determining the initial activity list based on one or more susceptibility factors, the external data, the desired arrival time and the vehicle dynamics; and
outputting the updated initial activity list to one or more users.

8. The method of claim 1, wherein the one or more sensors further comprises of radio frequency-based proximity sensors, sound-based proximity sensors, accelerometers, camera and GPS.

9. The method of claim 1, further comprising:
measuring a cognitive state of one or more users; and
updating the initial activity list and outputting the updated initial activity list based on the cognitive state of the one or more users.

10. The method of claim 9, wherein the cognitive state of the user further comprises of happy, sad, sleepy, angry and tired.

11. A computer system for recommending an activity during travel by an autonomous vehicle, the computer system comprising: one or more computer processors; one or more computer readable storage devices; and program instructions stored on the one or more computer readable storage devices for execution by at least one of the one or more computer processors, the stored program instructions comprising: program instructions to receive a request for a travel destination and a desired arrival time for a traveler on an autonomous vehicle; program instructions to determine a route to the travel destination;
program instructions to retrieve external data based on the route; program instructions to calculate and output an initial activity list based on the external data, energy consumption rate of the autonomous vehicle as required by each individual activity as part of the initial activity list, habit and propensity of the traveler and the route, wherein the initial activity list consists of jogging, rowing and running;
program instructions to measure vehicle dynamics based on one or more motion sensors of an autonomous vehicle; and program instructions to update the initial activity list and output the updated initial activity list based on the vehicle dynamics, energy consumption rate of the autonomous vehicle as required by each individual activity as part of the updated initial activity list and changing road conditions.

12. The computer system of claim 11, wherein determining the route to the travel destination further comprises:
program instructions to retrieve one or more routes to the travel destination; and
program instructions to select one route from the one or more routes based on the desired arrival time.

13. The computer system of claim 11, wherein retrieving external data further comprises of weather-related, traffic related and road conditions.

14. The computer system of claim 11, wherein calculating and outputting the initial activity list further comprises:
program instructions to determine the initial activity list based on one or more susceptibility factors, the external data and the desired arrival time; and
program instructions to output the initial activity list to one or more users.

15. The computer system of claim 14, wherein the one or more susceptibility factors further comprises of $\alpha$, $\beta$ and $\gamma$ wherein are $\alpha$, $\beta$ and $\gamma$ are the one or more susceptibility factors for the activity list associated movements along X, Y and Z axes, respectively.

16. The computer system of claim 11, wherein measuring the vehicle dynamics further comprises:
program instructions to retrieve data from one or more sensors wherein the one or more sensors are capable of detecting forces along x, y and z axis of the vehicle.

17. The computer system of claim 11, wherein updating the initial activity list and outputting the updated initial activity list based on the vehicle dynamics further comprises:
program instructions to determine the initial activity list based on one or more susceptibility factors, the external data, the desired arrival time and the vehicle dynamics; and
program instructions to output the initial activity list to one or more users.

18. The computer system of claim 11, wherein the one or more sensors further comprises of radio frequency-based proximity sensors, sound-based proximity sensors, accelerometers, camera and GPS.

19. The computer system of claim 11, further comprising:
program instructions to measure a cognitive state of one or more users; and
program instructions to update the initial activity list and output the updated initial activity list based on the cognitive state of the one or more users.

20. The computer system of claim 19, wherein the cognitive state of the user further comprises of happy, sad, sleepy, angry and tired.

\* \* \* \* \*